United States Patent [19]

Goldmann et al.

[11] Patent Number: 4,555,512

[45] Date of Patent: Nov. 26, 1985

[54] CIRCULATION-ACTIVE NOVEL CHROMONE- AND THIOCHROMONE-SUBSTITUTED 1,4-DIHYDROPYRIDINE-LACTONES

[75] Inventors: Siegfried Goldmann; Friedrich Bossert, both of Wuppertal; Matthias Schramm, Cologne; Günter Thomas; Rainer Gross, both of Wuppertal, all of Fed. Rep. of Germany

[73] Assignee: Bayer Aktiengesellschaft, Leverkusen, Fed. Rep. of Germany

[21] Appl. No.: 589,614

[22] Filed: Mar. 14, 1984

[30] Foreign Application Priority Data

Mar. 25, 1983 [DE] Fed. Rep. of Germany ....... 3311003

[51] Int. Cl.[4] .............. A61K 31/435; C07D 491/048
[52] U.S. Cl. .................... 514/302; 546/115; 544/127; 514/234; 514/236
[58] Field of Search ............ 546/115; 544/127; 514/234, 236, 302

Primary Examiner—Paul R. Michl
Assistant Examiner—Alex H. Walker
Attorney, Agent, or Firm—Sprung Horn Kramer & Woods

[57] ABSTRACT

Dihydropyridines of the formula

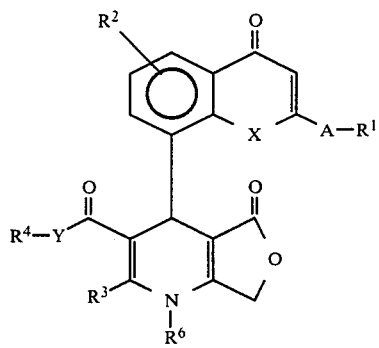

in which
$R^1$, $R^2$, $R^5$ and $R^6$ can be hydrogen or various halogen or organic radicals,
$R^4$ is an optionally substituted hydrocarbon radical,
A is a direct bond, a $C_1$–$C_{20}$-alkylene chain or a $C_2$–$C_{20}$-alkenylene chain, which chains are optionally interrupted by O or S
X is O or S, and
Y is a direct bond, O, S, —NH—or—N-alkyl with 1 to 8 C atoms
or a pharmaceutically acceptable salt, are useful as cardiotonic agents for improving heart contractility, antihypotonic agents, for lowering the blood sugar level, for detumescing mucous membranes and for influencing the salt and/or liquid balance.

13 Claims, No Drawings

CIRCULATION-ACTIVE NOVEL CHROMONE- AND THIOCHROMONE-SUBSTITUTED 1,4-DIHYDROPYRIDINE-LACTONES

The present invention relates to new 1,4-dihydropyridines, several processes for their preparation and their use in medicaments, in particular in medicaments which influence the circulation.

The new dihydropyridines are characterised by the following general formula (I):

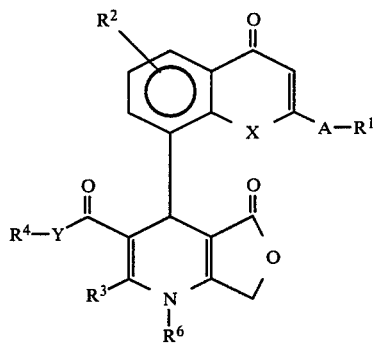

in which
$R^1$ represents hydrogen, a straight-chain, cyclic or branched aliphatic hydrocarbon radical with 1 to 10 C atoms, a carboxylic acid alkyl ester (alkyl radical with 1 to 10 C atoms), or an aromatic or heteroaromatic radical, which optionally can be substituted by one to 5 identical or different substituents from the group comprising halogen, alkyl (1 to 10 C atoms), alkoxy (1 to 10 C atoms), alkylthio (1 to 10 C atoms, alkylsulphinyl (1 to 10 C atoms), cyano, hydroxyl, nitro, mono- or poly-fluoroalkyl (1 to 5 C atoms), mono- or poly-fluoroalkoxy (1 to 5 C atoms), mono- or poly-fluoroalkylthio (1 to 5 C atoms), amino, monoalkylamino (1 to 5 C atoms) and dialkylamino (in each case 1 to 5 C atoms), $R^2$ represents 1 to 3 halogen atoms or hydrogen, $R^4$ represents a straight-chain, branched or cyclic, saturated or unsaturated hydrocarbon radical with 1 to 20 C atoms, which is optionally substituted by alkoxy with 1 to 10 C atoms, alkylthio with 1 to 10 C atoms, alkylsulphinyl with 1 to 10 C atoms, trialkylsilyl with in each case 1 to 6 C atoms, halogen, cyano, hydroxyl, amino, alkylamino with 1 to 6 C atoms, dialkylamino with in each case 1 to 6 C atoms, morpholinyl, piperidyl, piperazinyl, nitro, nitrate, aryl or heteroaryl, whereby the aryl- or heteroaryl radical can optionally be substituted by 1 to 3 identical or different substituents from the group comprising halogen, alkyl with 1 to 6 C atoms, alkoxy with 1 to 6 C atoms, alkylthio with 1 to 6 C atoms, alkylsulphinyl with 1 to 6 C atoms, alkylsulphonyl with 1 to 6 C atoms, hydroxyl, cyano, nitro, amino, alkylamino with 1 to 6 C atoms, dialkylamino with in each case 1 to 6 C atoms, mono- or poly-fluoroalkyl with 1 to 6 C atoms and mono- or poly-fluoroalkoxy with 1 to 6 C atoms, $R^5$ represents hydrogen or a straight-chain, branched or cyclic, saturated or unsaturated aliphatic alkyl radical with 1 to 10 C atoms, which optionally contains one or two identical or different hetero chain members from the group comprising O, CO, NH, N-alkyl with 1 to 8 C atoms, S and $SO_2$, and is optionally substituted by halogen, nitro, cyano, azido, hydroxyl, aryl, heteroaryl, amino or monoalkylamino or dialkylamino with in each case 1 to 6 C atoms, $R^6$ represents hydrogen or a straight-chain or branched alkyl radical (with 1 to 20 C atoms), which is optionally substituted by alkoxy (with 1 to 10 C atoms), halogen or morpholino, A represents a direct bond, an alkylene chain (1 to 20 C atoms) or an alkenylene chain (2 to 20 C atoms), the chains being optionally interrupted by O or S, X represents O or S and Y represents a direct bond, O, S, —NH— or N-alkyl (with 1 to 8 C atoms), in the form of isomers, isomer mixtures, racemates and optical antipodes, and their pharmaceutically acceptable salts.

Examples of salts which may be mentioned are hydrochlorides, hydrogen sulphates, sulphates, hydrogen phosphates, acetates, maleates, benzoates, citrates, tartrates and lactates.

Compounds of the general formula (I) which are of particular interest are those in which $R^1$ represents hydrogen, a straight-chain, cyclic or branched aliphatic hydrocarbon with 1 to 8 C atoms, a carboalkoxy radical with 1 to 8 C atoms in the alkyl radical, phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl, it being possible for the aryl and heteroaryl radicals optionally to contain one to 5 identical or different substituents from the group comprising fluorine, chlorine, bromine, iodine, alkyl (1 to 8 C atoms), alkylthio (1 to 8 C atoms), alkylsulphinyl (1 to 8 C atoms), cyano, hydroxyl, nitro, mono- or poly-fluoroalkyl (1 to 4 C atoms), mono- or poly-fluoroalkoxy (1 to 4 C atoms), mono- or poly-fluoroalkylthio (1 to 4 C atoms), amino, monoalkylamino (1 to 5 C atoms) and dialkylamino (in each case 1 to 5 C atoms), $R^2$ represents hydrogen or one to three fluorine or chlorine atoms, $R^4$ represents a straight-chain, branched or cyclic saturated or unsaturated hydrocarbon radical with 1 to 18 C atoms, which is optionally substituted by alkoxy (with 1 to 8 C atoms), alkylthio (with 1 to 8 C atoms), alkylsulphinyl (with 1 to 8 C atoms), trialkylsilyl (with in each case 1 to 5 C atoms), Cl, Br, I, F, cyano, hydroxyl, amino, alkylamino (with 1 to 5 C atoms), dialkylamino (with in each case 1 to 5 C atoms), morpholinyl, piperidyl, piperazinyl, nitro, nitrate, phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, indolyl or quinazolyl, it being possible for the aromatics or heteroaromatics mentioned optionally to be substituted by 1 to 3 identical or different substituents from the group comprising F, Cl, Br, alkyl (with 1 to 5 C atoms), alkoxy (with 1 to 5 C atoms), alkylthio (with 1 to 4 C atoms) and alkylsulphinyl (with 1 to 4 C atoms).

$R^5$ represents hydrogen or a straight-chain, branched or cyclic, saturated or unsaturated aliphatic alkyl radical (1 to 8 C atoms), which optionally contains one or two identical or different hetero chain members from the group comprising O, CO, S and N-alkyl (1 to 6 C atoms), and is optionally substituted by halogen, nitro, cyano, hydroxyl, amino or monoalkylamino or dialkylamino (with in each case 1 to 5 C atoms), R$^6$ represents hydrogen or a straight-chain or branched alkyl radical (with 1 to 16 C atoms), which is optionally substituted by alkoxy (with 1 to 8 C atoms), halogen or morpholino, A represents a direct bond, an alkylene chain (1 to 18 C atoms) or an alkenylene chain (2 to 18 C atoms), the chains being optionally interrupted by O or S, X represents O or S and Y represents a direct bond, O, S, —NH— or -N(alkyl)- (with 1 to 6 C atoms).

Compounds of the general formula (I) which may be mentioned as preferred are those in which R$^1$ represents hydrogen, a straight-chain, cyclic or branched aliphatic hydrocarbon radical with 1 to 7 C atoms, a carboalkoxy radical with 1 to 6 C atoms in the alkyl radical, phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, indolyl, benzimidazolyl or quinazolyl, it being possible for the aryl and heteroaryl radicals optionally to contain one to 4 identical or different substituents from the group comprising fluorine, chlorine, bromine, alkyl (1 to 6 C atoms), alkylthio (1 to 6 C atoms), alkylsulphinyl (1 to 6 C atoms), cyano, hydroxyl, nitro, mono- or poly-fluoroalkyl (1 to 3 C atoms), mono- or poly-fluoroalkoxy (1 to 3 C atoms), amino, monoalkylamino (1 to 4 C atoms) and dialkylamino (in each case 1 to 4 C atoms), R$^2$ represents hydrogen or one to three fluorine atoms, R$^4$ represents a straight-chain, branched or cyclic, saturated or unsaturated hydrocarbon radical with 1 to 12 C atoms, which is optionally substituted by alkoxy (with 1 to 6 C atoms), alkylthio (with 1 to 6 C atoms), alkylsulphinyl (with 1 to 6 C atoms, trialkylsilyl (with in each case 1 to 3 C atoms), Cl, Br, F, cyano, hydroxyl, amino, alkylamino (with 1 to 4 C atoms), dialkylamino (with in each case 1 to 4 C atoms), morpholinyl, piperidyl, piperazinyl, nitro, nitrate, phenyl, naphthyl, thienyl, furyl, pyrryl, imidazolyl, oxazolyl, thiazolyl, pyridyl, pyrimidyl, pyrazinyl or indolyl, it being possible for the aromatics or heteroaromatics mentioned optionally to be substituted by 1 to 3 identical or different substituents from the group comprising F, Cl, Br, alkyl (with 1 to 4 C atoms), alkoxy (with 1 to 4 C atoms), alkylthio (with 1 to 3 C atoms) and alkylsulphinyl (with 1 to 3 C atoms), R$^5$ represents hydrogen or a straight-chain, branched or cyclic, saturated or unsaturated aliphatic alkyl radical (1 to 6 C atoms), which optionally contains one or two identical or different hetero chain members from the group comprising O, CO, S and N-alkyl (1 to 4 C atoms), and which is optionally substituted by halogen, nitro, cyano, hydroxyl, amino or monoalkylamino or dialkylamino (with in each case 1 to 4 C atoms), R$^6$ represents hydrogen or a straight-chain or branched alkyl radical (with 1 to 12 C atoms), which is optionally substituted by alkoxy (with 1 to 6 C atoms), halogen or morpholino, A represents a direct bond, an alkylene chain (1 to 16 C atoms) or an alkenylene chain (2 to 14 C atoms), the chains being optionally interrupted by O or S, X represents O or S and Y represents a direct bond, O, S, —NH— or -N(alkyl)- (with 1 to 4 C atoms).

The compounds of the general formula (I) according to the invention can be prepared by a process in which (A) aldehydes of the general formula (II)

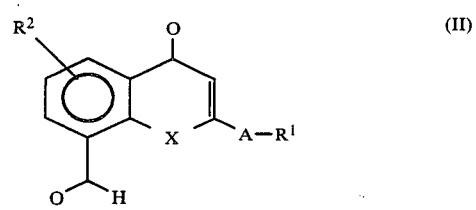

in which

R$^1$, R$^2$, A and X have the abovementioned meaning, are reacted with enamines of the general formula (III)

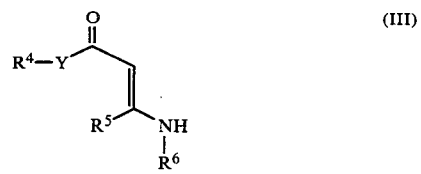

in which

R$^4$, R$^5$, R$^6$ and Y have the abovementioned meaning and ketones of the general formula (IV)

in which

R$^7$ represents an alkyl chain with 1 to 6 C atoms and Z represents halogen or —O—B, wherein B represents an alcohol-protective group, such as

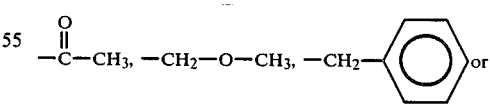

—Si(Alkyl)$_3$ if appropriate in the presence of an inert organic solvent at temperatures between 20° and 150° C., and, if Z=—O—B, the protective group is removed with suitable agents, or (B) aldehydes of the general formula (II) in which R$^1$, R$^2$, and X have the abovementioned meaning, are reacted with ketones of the general formula (V)

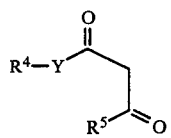

in which
R⁴ and R⁵ have the abovementioned meaning and enamines of the general formula (VI)

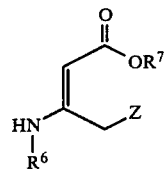

in which
R⁶, R⁷ and Z have the abovementioned meaning, if appropriate in the presence of inert organic solvents at temperatures between 20° and 150° C. and, if Z=O—B, B having the abovementioned meaning, the protective group is then removed with suitable agents, or (C) ylidene compounds of the general formula (VII)

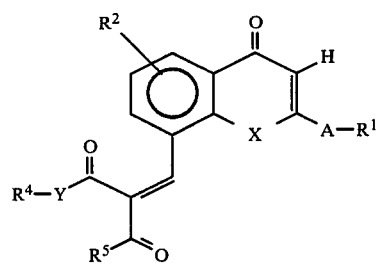

in which
R¹, R², R⁴, R⁵, A, X and Y have the abovementioned meaning, are reacted with enamines of the general formula (VI) in which R⁶, R⁷ and Z have the abovementioned meaning, if appropriate in the presence of inert organic solvents at temperatures between 20° and 150° C. and, if Z=O—B, B having the abovementioned meaning, the protective group is then split off with suitable agents, or (D) aldehydes of the general formula (II) in which R¹, R², A and X have the abovementioned meaning, are reacted with ketones of the general formula (V) in which R⁴, R⁵ and Y have the abovementioned meaning and with tetronic acid amides of the general formula (VIII)

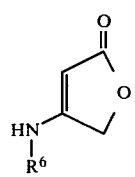

in which
R⁶ has the abovementioned meaning, if appropriate in the presence of inert organic solvents at temperatures between 20° and 150° C., or (E) benzylidene compounds of the general formula (IX)

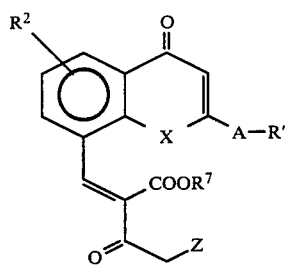

in which
R¹, R², R⁷, A, X and Z have the abovementioned meaning, are reacted with enamines of the general formula (III) in which R⁴, R⁵, R⁶ and Y have the abovementioned meaning, if appropriate in inert organic solvents at temperatures from 20° to 150° C. and, if Z=O—B, B having the abovementioned meaning, the protective group is split off with suitable agents.

Examples which may be mentioned of suitable processes for splitting off the protective group in processes A, B, C and E are: acid-catalyzed splitting off (for example if

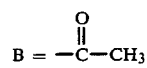

or —CH₂—O—CH₃), basic splitting off (for example if

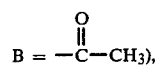

hydrogenolytic splitting off (for example if

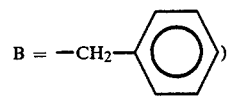

or splitting off with fluoride (for example if B=Si-(alkyl)₃).

The splitting off can be carried out at temperatures from 0° to 150° C.

Process variants A, C and E are preferred.

The reactants can be used in any desired proportions relative to one another, and equimolar amounts are preferred. However, the compounds of the formulae (III), (V) and (VI) can also be employed in an excess of up to 3 moles.

The reaction temperatures of all process variants are preferably 30° to 120° C., in particular the boiling points of the solvents used.

If the reaction is carried out in the presence of organic solvents, all the inert solvents are suitable, such as, for example, alcohols, acetic acid, benzene and/or toluene.

The aldehydes of the formula (II) used for the preparation are new and can be prepared, if X=S, by reducing thiochromones of the formula

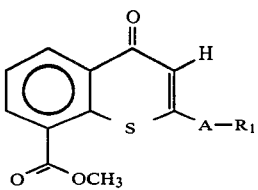

in which

R$_1$, R$_2$ and A have the meanings already mentioned, to benzyl alcohols which

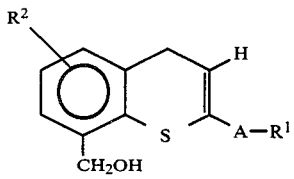

is oxidized to aldehydes with oxidizing agents.

Thiochromones used as starting substances are known and can be prepared by known processes (Bossert, Lieb. Ann. 680, 40 (1964)).

Inert organic solvents can be used for the reduction to the benzyl alcohol, for example ethers, such as, for example, dioxane, diethyl ether, tetrahydrofuran or dimethoxyethane, or aromatics, such as, for example, toluene or benzene. Examples of reducing agents which may be mentioned are alkali metal aluminum hydrides, such as, for example, LiAlH$_4$, or alkyl-aluminum hydrides, such as, for example, diisobutyl-aluminum hydride.

This process is preferably carried out in a temperature range from $-100°$ C. to $+60°$ C., in particular in a range from $-60°$ C. to $+30°$ C.

The reaction is usually carried out under normal pressure, but can also be carried out under increased pressure.

The reducing agent is added in amounts customary to the expert, preferably in amounts of at least four and at most 8 equivalents of hydride.

The same solvents as used in the reduction can be used for the oxidation of the benzyl alcohol to the aldehyde, and in addition halogenated hydrocarbons, such as chloroform and methylene chloride, or ketones, such as, for example, acetone.

The transition metal oxides usually employed for oxidations, but preferably manganese dioxide, can be used as the oxidizing agent.

The oxidation is usually carried out in a temperature range from $-30°$ to $+200°$ C., preferably at the boiling point of the particular solvent. The oxidation is usually carried out under normal pressure, but can also be carried out under increased pressure.

The oxidizing agent can be employed in amounts of 3 to 20, preferably 5 to 10, oxidation equivalents. It may also be advantageous to add fresh oxidizing agent to the reaction mixture from time to time.

If $X=O$, chromones of the formula (X)

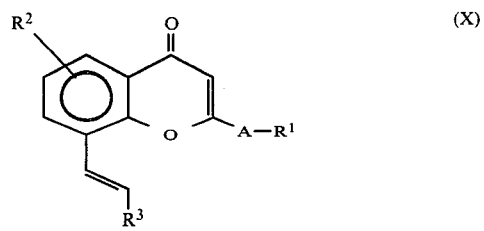

in which

R$^1$, R$^2$ and Y have the abovementioned meaning, with the restriction that A is not an alkenylene chain or contains sulphur and R$^3$ represents hydrogen or alkyl (with 1 to 10 C atoms), are reacted with ozone in the presence of inert organic solvents and the mixture is then worked up by reduction.

8-Alkenylchromones used as starting substances are known and can be prepared by known processes (U.S. Pat. No. 3,350,411, compare also Synthesis 1982, 221).

Inert solvents which may be mentioned for the ozonolysis are: chlorinated hydrocarbons, such as, for example, methylene chloride, chloroform or carbon tetrachloride, esters, such as, for example, ethyl acetate, alcohols, such as, for example, methanol or ethanol and acids, such as, for example, formic acid or acetic acid.

The ozonolysis is carried out at $-100°$ C. to 20° C., but preferably at $-80°$ C. to $-30°$ C., with subsequent working up by reduction, for example with dimethyl sulphide, with zinc dust, by catalytic hydrogenation or with sodium dithionite.

Only one mole of ozone is used per mole of chromone (X), in order to prevent splitting of further double bonds.

Enamines of the general formula (III) used for the preparation are known and can be prepared by known processes (compare A. C. Cope, J. Am. Chem. Soc. 67, 1017 (1945)).

The β-Keto esters of the general formula (IV) used for the preparation are known and can be prepared by known processes (compare Gelin, Pallet, Synth. Comm 1980, 805; and Tetrahedron 34, 1453 (1978)). Or: commercially available from LONZA AG (Z=Cl).

The ketones having the structure (V) used for the preparation are known and can be prepared by known processes: for example, if Y=O, D. Borrmann, Umsetzung von Diketen mit Alkoholen, Phenolen und Mercaptanen (Reaction of diketene with alcohols, phenols and mercaptans) in Houben-Weyl, Methoden der Organischen Chemie (Methods of Organic Chemistry), Volume VII, 14, 230 et seq. (1968) and Y. Dikawa, K. Sugano and O. Yonemitsu, J. Org. Chem. 43, 2087 (1978).

The β-aminocrotonates of the general formula (VI) used for the preparation can be prepared by known processes (compare A. C. Cope, J. Amer. Chem. Soc. 67, 1017 (1945)).

The benzylidene compounds having the structure (VII) used for the preparation are new, but can be prepared by known processes (compare G. Jones, "The Knoevenagel Condensation", in Org. Reactions Volume XV, 204 et seq. (1967)).

The compounds according to the invention display a valuable pharmacological action spectrum which could not be predicted. They can be used as cardiotonic agents for improving heart contractility. Moreover, since they increase the flow of Ca++ into the cells, they can be used as antihypotonic agents, for lowering the blood sugar level, for detumescing mucous membranes and for influencing the salt and/or liquid balance.

The compounds according to the invention can be converted in a known manner into the customary formulations, such as tablets, capsules, dragees, pills, granules, aerosols, syrups, emulsions, suspensions and solutions, using inert non-toxic, pharmaceutically suitable excipients or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, in particular perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc, can be co-used when making tablets. In the case of aqueous suspensions and/or elixirs which are intended for oral use, the active compounds can be mixed with various flavor-improving agents or colorants in addition to the abovementioned auxiliary substances.

In the case of parenteral use, solutions of the active compounds, employing suitable liquid excipients, can be used.

In general, it has proved advantageous, in the case of intravenous administration, to administer amounts of about 0.001 to 1 mg/kg, preferably about 0.01 to 0.5 mg/kg, of body weight daily to achieve effective results, and in the case of oral administration, the dosage is about 0.01 to 20 mg/kg, preferably 0.1 to 10 mg/kg, of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, and its nature of the formulation of the medicament and the time or interval over which the administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day. The same dosage range is envisaged for administration in human medicine. The above statements also apply here in the general sense.

EXAMPLE 1

Ethyl 2-methyl-4-(4-oxo-2-phenyl-4H-thiochromen-8-yl)-5-oxo-1,4,5,7-tetrahydrofuro[3,4-b]pyridine-3-carboxylate (a) with γ-chloroacetoacetate 10 millimoles each of 4-oxo-2-phenyl-4H-thiochromene-8-carboxaldehyde, ethyl 3-aminocrotonate and methyl γ-chloroacetoacetate are boiled under reflux in 30 ml of ethanol overnight. After cooling, the mixture is filtered with suction.

Melting point: 271°–273° C.

(b) with 4-acetoxyacetoacetate

The mixture is as under (a), but with ethyl 4-acetoxyacetoacetate instead of the γ-chloroacetoacetate. After reflux overnight, 2 ml of saturated ethanolic HCl are added, the mixture is boiled under reflux for 1 hour, cooled and filtered with suction and the product was recrystallized from a large amount of ethanol.

Melting point: 271°–273° C.

EXAMPLE 2 (Process Variant B)

Ethyl 2-methyl-4-[2-(3-chlorophenyl)-4-oxo-4H-chromen-8-yl]-5-oxo-1,4,5,7-tetrahydrofuro[3,4-b]pyridine-3-carboxylate Preparation of the intermediate:

Ethyl 3-amino-4-acetoxy-crotonate (VI, $R^6$=H, $R^7$=—$C_2H_5$,

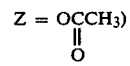
)

A solution of ethyl 4-acetoxy-3-keto-butyrate and catalytic amounts of p-toluenesulphonic acid in toluene is heated, using a water separator, and ammonia is passed in until the formation of water has ended.

The mixture is washed with water, dried and concentrated and the residue is distilled (0.2 mm/90° C.).

Melting point: 51° C.

10 millimoles each of 2-(3-chlorophenyl)-4-oxo-4H-chromene-8-carboxaldehyde, ethyl acetoacetate and ethyl 3-amino-4-acetoxy-crotonate are boiled in 30 ml of ethanol overnight, 2 ml of saturated ethanolic HCl are then added and the mixture is heated for a further hour. The mixture is concentrated on a rotary evaporator and crystallized.

Melting Point: >260° C.

Mass spectrum: 477 (100%), 448, 404, 256, 222.

EXAMPLE 3 (Process variant C)

Methyl 2-methyl-4-(2-cyclohexyl-4-oxo-4H-chromen-8-yl)-5-oxo-1,4,5,7-tetrahydrofuro[3,4-b]pyridine-3-carboxylate 10 millimoles each of methyl 1-(2-cyclohexyl-4-oxo-4H-chromen-8-yl)-1-buten-3-oxo-2-carboxylate (VII, $A-R^1 = $ 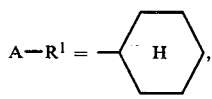, $R^2=H$, $Y-R^4=OCH_3$, $X=O$, $R^5=CH_3$) and ethyl 3-amino-4-acetoxycrotonate (from Example 2) are boiled under reflux in 30 ml of ethanol overnight, 2 ml of saturated ethanolic HCl are then added and the mixture was boiled for 1 hour and concentrated.

Melting point: 182°–185° C.

EXAMPLE 4 (Process variant D)

Methyl 2-methyl-4-(4-oxo-2-phenyl-4H-thiochromen-8-yl)-5-oxo-1,4,5,7-tetrahydrofuro[3,4-b]pyridine-3-carboxylate Preparation of the intermediate:

Tetronic acid amide (VIII, $R^6=H$)

8 g of anhydrous $K_2CO_3$ are added to 0.2 mole of ethyl 3-amino-4-acetoxy-crotonate (from Example 2), dissolved in 600 ml of dry methanol, and the mixture is boiled under reflux for 40 minutes. After cooling, 10 g of $NH_4Cl$ are added, the mixture is concentrated on a rotary evaporator and the residue is boiled up with methanol. Tetronic acid amide crystallizes out of the methanol solution (melting point: 161°–163° C.).

10 millimoles each of methyl 1-(4-oxo-2-phenyl-4H-thiochromen-8-yl)-1-buten-3-oxo-2-carboxylate (VII, $A-R^1 = $ 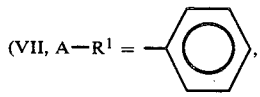, $R^2=H$, $X=S$, $Y-R^4=OCH_3$, $R^5=CH_3$) and tetronic acid amide are boiled under reflux in 30 ml of ethanol overnight and the mixture is chromatographed.

Melting point: 270° C.

Mass spectrum: 445, 443, 238, 224, 208.

EXAMPLE 5 (Process variant E)

Methyl 2-methyl-4-(2-octyl-4-oxo-4H-chromen-8-yl)-5-oxo-1,4,5,7-tetrahydrofuro[3,4-b]pyridine-3-carboxylate 10 millimoles each of methyl 1-(2-octyl-4-oxo-4H-chromen-8-yl)-1-butene-4-chloro-3-oxo-3-carboxylate and methyl 3-aminocrotonate are heated under reflux in 30 ml of ethanol overnight, 2 ml of saturated ethanolic HCl are added and the mixture is heated for a further hour. The mixture is cooled and concentrated.

Melting point: 129°–132° C.

The following compounds are prepared analogously to Example 1b:

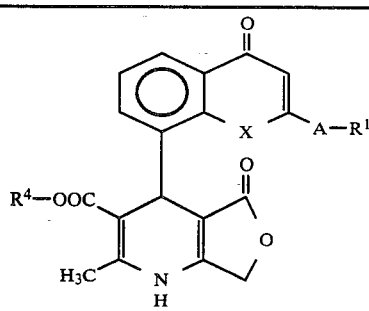

| Example | A—R¹ | R⁴ | X | Melting point (°C.) |
|---|---|---|---|---|
| 6 | phenyl | —CH₃ | S | >270 |
| 7 | " | —(CH₂)₂—CH₃ | S | 175–80 |
| 8 | " | —CH₂—CH=CH₂ | S | 248–51 |
| 9 | " | —C₄H₉ | S | >265 |
| 10 | " | —(CH₂)₇—CH₃ | S | 114 |
| 11 | " | —CH₂—cyclohexyl | S | >290 |
| 12 | " | —CH₂—CH₂—OCH₃ | S | 268–70 |
| 13 | " | —CH(CH₃)₂ | S | 261–63 |
| 14 | " | —C(CH₃)₃ | S | >260 (decomposition) |
| 15 | " | cyclohexyl | S | >260 |
| 16 | " | cyclopentyl | S | >260 |
| 17 | " | —H₃C—(2-SCH₃-phenyl) | S | 232–35 |
| 18 | " | —H₃C—phenyl | S | >275 |
| 19 | " | —CH₂—CH₂—Si(CH₃)₃ | S | >270 |
| 20 | " | —(CH₂)₂—SCH₃ | S | >270 |
| 21 | " | —CH(CH₃)—CH₂—CH₃ | S | >300 |

-continued

| Example | A—R¹ | R⁴ | X | Melting point (°C.) |
|---|---|---|---|---|
| 22 | " | —CH₃ | O | >260 |
| 23 | (2-Cl-phenyl) | —(CH₂)₇—CH₃ | O | 218-20 |
| 24 | (cyclohexyl, H) | —C₂H₅ | O | 212-15 |
| 25 | " | —CH₃ | O | 182-185 |
| 26 | (phenyl) | —C₂H₅ | O | >280 |
| 27 | " | —C₄H₉ | O | >280 |
| 28 | —(CH₂)₈—CH₃ | —C₂H₅ | O | 172-175 |
| 29 | (pyridyl) | —C₂H₅ | O | >270 |
| 30 | —(CH₂)₈—CH₃ | —CH₃ | O | 129-132 |
| 31 | —C(CH₃)₃ | —C₂H₅ | O | >270 |
| 32 | —COOC₂H₅ | —C₂H₅ | O | 140-144 |
| 33 | (thienyl) | —C₂H₅ | O | >270 |
| 34 | —(CH₂)₄—CH₃ | —C₂H₅ | O | 219-221 |
| 35 | " | —CH₃ | O | 222-225 |
| 36 | (3-Cl-phenyl) | —C₂H₅ | O | >280 |
| 37 | " | —CH₃ | S | >270 |

TEST OF THE POSITIVE INOTROPIC EFFECT

Test procedure

The left atria of guinea pig hearts are isolated and suspended in an organ bath which contains an isotonic mineral salt solution is adjusted to correspond with the ionic medium and the pH value of body fluids and also contains suitable nutrients. This organ bath is aerated with a gas mixture consisting of oxygen and carbon dioxide, the carbon dioxide content being such that the pH value of the organ bath remains constant. The left atria are fixed in the organ bath, the tension is recorded by means of a force transducer, a specific basic tonus being adjusted. Then the left atria are continuously electrically excited at specific intervals and the resulting contractions are recorded. The recording of the contractions is still carried out after the addition of the active compound. An increase of at least 25% in the contractions is considered to be a significant positive inotropic effect.

Of particular significance are those compounds of the general formula (I) which, in the following test procedure, already begin to show a positively inotropic effect on the left atria of the isolated guinea-pig hearts at a concentration of $10^{-5}$ g/ml.

The following may be mentioned as examples: Δdp/dt

Example 1 +35%
Example 5 +42%
Example 7 +41%
Example 9 +57%

It is understood that the specification and examples are illustrative but not limitative of the present invention and that other embodiments within the spirit and scope of the invention will suggest themselves to those skilled in the art.

We claim:

1. A dihydropyridine of the formula

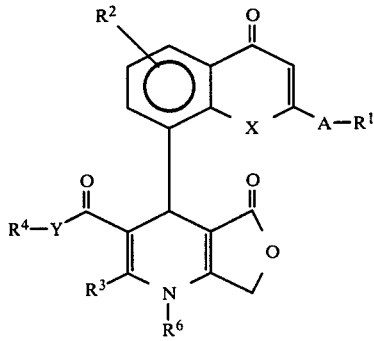

(I)

in which

R¹ represents hydrogen, a straight-chain, cyclic or branched aliphatic hydrocarbon radical with 1 to 10 C atoms, a carboxylic acid alkyl ester with an alkyl radical of 1 to 10 C atoms, an aromatic or a heteroaromatic radical which optionally can be substituted by one to 5 identical or different substituents from the group comprising halogen, $C_1$-$C_{10}$-alkyl, $C_1$-$C_{10}$-alkoxy, $C_1$-$C_{10}$-alkylthio, $C_1$-$C_{10}$-alkylsulphinyl, cyano, hydroxyl, nitro, mono- or poly-fluoro-$C_1$-$C_5$-alkyl, mono- or poly-fluoro-$C_1$-$C_5$-alkoxy, mono- or poly-fluoro-$C_1$-$C_5$- alkylthio, amino, mono-$C_1$-$C_5$-alkylamino and di-$C_1$-$C_5$-alkylamino, $R^2$ represents one to three halogen atoms or hydrogen, $R^4$ represents a straight-chain, branched or cyclic, saturated or unsaturated hydrocarbon radical with 1 to 20 C atoms, which is optionally substituted by alkoxy with 1 to 10 C atoms, alkylthio with 1 to 10 C atoms, alkylsulphinyl with 1 to 10 C atoms, trialkylsilyl with in each case 1 to 6 atoms, halogen, cyano, hydroxyl, amino, alkylamino with 1 to 6 C atoms, dialkylamino with in each case 1 to 6 C atoms, morpholinyl, piperidyl, piperazinyl, nitro, nitrate, aryl or heteroaryl either of which can optionally be substituted by 1 to 3 identical or different substituents from the group comprising halogen, alkyl with 1 to 6 C atoms, alkoxy with 1 to 6 C atoms, alkylthio with 1 to 6 C atoms, alkylsulphinyl with 1 to 6 C atoms, alkylsulphonyl with 1 to 6 C atoms, hydroxyl, cyano, nitro, amino, alkylamino with 1 to 6 C atoms, dialkylamino with in each case 1 to 6 C atoms, mono- or poly-fluoroalkyl with 1 to 6 C atoms and mono- or poly-fluoroalkoxy with 1 to 6 C atoms, $R^5$ represents hydrogen or a straight-chain, branched or cyclic, saturated or unsaturated aliphatic alkyl radical with 1 to 10 C atoms, which optionally contains one or two identical or different hetero chain members from the group comprising O, CO, NH, N-alkyl with 1 to 8 C atoms, S and $SO_2$, and is optionally substituted by halogen, nitro, cyano, azido, hydroxyl, aryl, heteroaryl, amino or monoalkylamino or dialkylamino with in each case 1 to 6 C atoms, $R^6$ represents hydrogen or a straight-chain or branched $C_1$-$C_{20}$-alkyl radical, which is optionally substituted by $C_1$-$C_{10}$-alkoxy, halogen or morpholino, A represents a direct bond, a $C_1$-$C_{20}$-alkylene chain or a $C_2$-$C_{20}$-alkenylene chain, which chains are optionally interrupted by O or S, X represents O or S and Y represents a direct bond, O, S, —NH— or —N—alkyl with 1 to 8 C atoms, or a pharmaceutically acceptable salt.

2. A compound or salt according to claim 1, in which $R^1$ represents hydrogen, a straight-chain, cyclic or branched aliphatic hydrocarbon radical with 1 to 8 C atoms, a carboalkoxy radical with 1 to 8 C atoms in the alkyl chain, phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl, it being possible for the aryl and heteroaryl radicals mentioned optionally to contain one to 5 identical or different substituents from the group comprising fluorine, chlorine, bromine, iodine, $C_1$-$C_8$-alkyl, $C_1$-$C_8$-alkylthio, $C_1$-$C_8$-alkylsulphinyl, cyano, hydroxyl, nitro, mono- or poly-fluoro-$C_1$-$C_4$-alkyl, mono- or poly-fluoroalkoxy with 1 to 4 C atoms, mono- or poly-fluoroalkylthio with 1 to 4 C atoms, amino, monoalkylamino with 1 to 5 C atoms and dialkylamino with in each case 1 to 5 C atoms, $R^2$ represents hydrogen or one to three fluorine or chlorine atoms, $R^4$ represents a straight-chain, branched or cyclic saturated or unsaturated hydrocarbon radical with 1 to 18 C atoms, which is optionally substituted by $C_1$-$C_8$-alkoxy, $C_1$-$C_8$-alkylthio, $C_1$-$C_8$-alkylsulphinyl, trialkylsilyl with in each case 1 to 5 C atoms, Cl, Br, I, F, cyano, hydroxyl, amino, alkylamino with 1 to 5 C atoms, dialkylamino with in each case 1 to 5 C atoms, morpholinyl, piperidyl, piperazinyl, nitro, nitrate, phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, indolyl or quinazolyl, it being possible for the aromatics or heteroaromatics mentioned optionally to be substituted by 1 to 3 identical or different substituents from the group comprising F, Cl, Br, $C_1$-$C_5$-alkyl, $C_1$-$C_5$-alkoxy, $C_1$-$C_4$-alkylthio and $C_1$-$C_4$-alkylsulphinyl, $R^5$ represents hydrogen or a straight-chain, branched or cyclic, saturated or unsaturated aliphatic $C_1$-$C_8$-alkyl radical, which optionally contains one or two identical or different hetero chain members from the group comprising O, CO, S or N-alkyl with 1 to 6 C atoms, and is optionally substituted by halogen, nitro, cyano, hydroxyl, amino or mono-$C_1$-$C_5$-alkylamino or dialkylamino with in each case 1 to 5 C atoms, $R^6$ represents hydrogen or a straight-chain or branched $C_1$-$C_{16}$-alkyl radical, which is optionally substituted by $C_1$-$C_8$-alkoxy, halogen or morpholino, A represents a direct bond, a $C_1$-$C_{18}$-alkylene chain or a $C_2$-$C_{18}$-alkenylene chain, which the chains are optionally interrupted by O or S, Y represents a direct bond, O, S, —NH— or -N(alkyl)- with 1 to 6 C atoms.

3. A compound or salt according to claim 1, in which $R^1$ represents hydrogen, a straight-chain, cyclic or branched aliphatic hydrocarbon radical with 1 to 7 C atoms, a carboalkoxy radical with 1 to 6 C atoms in the alkyl chain, phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, indolyl, benzimidazolyl or quinazolyl, it being possible for the aryl and heteroaryl radicals mentioned optionally to contain one to 4 identical or different substituents from the group comprising fluorine, chlorine, bromine, $C_1$-$C_6$-alkyl, $C_1$-$C_6$-alkylthio, $C_1$-$C_6$-alkylsulphinyl, cyano, hydroxyl, nitro, mono- or poly-fluoroalkyl with 1 to 3 C atoms, mono- or poly-fluoroalkoxy with 1 to 3 C atoms, amino, monoalkylamino with 1 to 4 C atoms and dialkylamino with in each case 1 to 4 C atoms, $R^2$ represents hydrogen or one to three fluorine atoms, $R^4$ represents a straight-chain, branched or cyclic, saturated or unsaturated hydrocarbon radical with 1 to 12 C atoms, which is optionally substituted by $C_1$-$C_6$-alkoxy, $C_1$-$C_6$-alkylthio, $C_1$-$C_6$-alkylsulphinyl, trialkylsilyl with in each case 1 to 3 C atoms, Cl, Br, F, cyano, hydroxyl, amino, alkylamino with 1 to 4 C atoms, dialkylamino with in each case 1 to 4 C atoms, morpholinyl, piperidyl, piperazinyl, nitro, nitrate, phenyl, naphthyl, thienyl, furyl, pyrryl, imidazolyl, oxazolyl, thiazolyl, pyridyl, pyrimidyl, pyrazinyl or indolyl, it being possible for the aromatics or heteroaromatics mentioned optionally to be substituted by 1 to 3 identical or different substituents from the group comprising F, Cl, Br, $C_1$–$C_4$-alkyl, $C_1$–$C_4$-alkoxy, $C_1$–$C_3$-alkylthio and $C_1$–$C_3$-alkylsulphinyl, $R^5$ represents hydrogen or a straight-chain, branched or cyclic, saturated or unsaturated aliphatic alkyl radical with 1 to 6 C atoms, which optionally contains one or two identical or different hetero chain members from the group comprising O, CO, S and N-alkyl with 1 to 4 C atoms, and is optionally substituted by halogen, nitro, cyano, hydroxyl, amino, mono-$C_1$–$C_4$-alkylamino or dialkylamino with in each case 1 to 4 C atoms, $R^6$ represents hydrogen or a straight-chain or branched $C_1$–$C_{12}$-alkyl radical, which is optionally substituted by $C_1$–$C_6$-alkoxy, halogen or morpholino, A represents a direct bond, a $C_1$–$C_{16}$-alkylene chain or a $C_2$–$C_{14}$-alkenylene chain, which the chains are optionally interrupted by O or S, and Y represents a direct bond, O, S, —NH— or -N(alkyl)- with 1 to 4 C atoms.

4. A compound according to claim 1 wherein such compound is ethyl 2-methyl-4-(4-oxo-2-phenyl-4H-thiochromen-8-yl)-5-oxo-1,4,5,7-tetrahydrofuro[3,4-b]pyridine-3-carboxylate of the formula

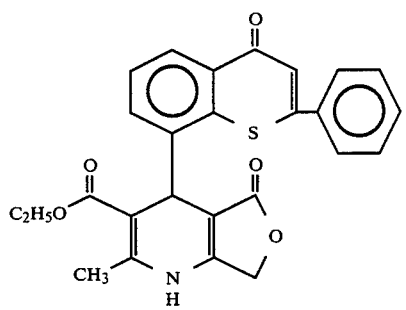

or a pharmaceutically acceptable salt thereof.

5. A compound according to claim 1 wherein such compound is methyl 2-methyl-4-(4-oxo-2-phenyl-4H-thiochromen-8-yl)-5-oxo-1,4,5,7-tetrahydrofuro[3,4-b]pyridine-3-carboxylate of the formula

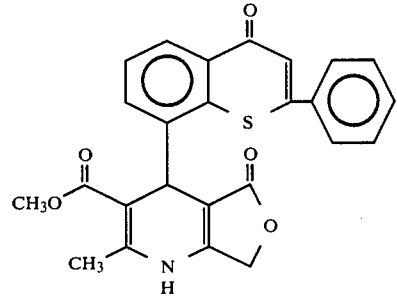

or a pharmaceutically acceptable salt thereof.

6. A compound according to claim 1 wherein such compound is n-octyl 2-methyl-4-(4-oxo-2-phenyl-4H-thiochromen-8-yl)-5-oxo-1,4,5,7-tetrahydrofuro[3,4-b]pyridine-3-carboxylate of the formula

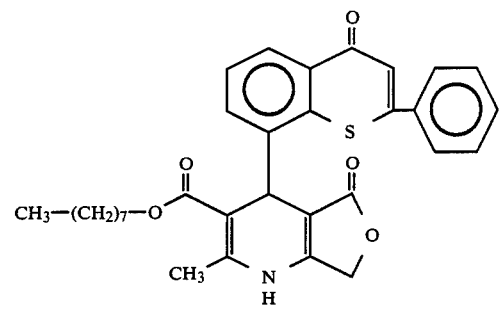

or a pharmaceutically acceptable salt thereof.

7. A compound according to claim 1 wherein such compound is isopropyl 2-methyl-4-(4-oxo-2-phenyl-4H-thiochromen-8-yl)-5-oxo-1,4,5,7-tetrahydrofuro [3,4-b]pyridine-3-carboxylate of the formula

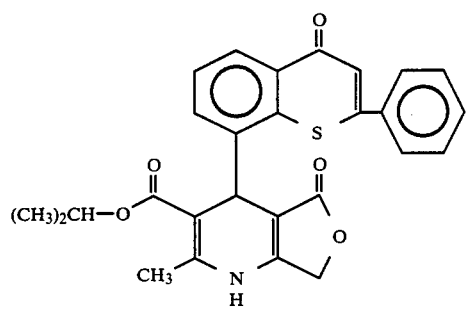

or a pharmaceutically acceptable salt thereof.

8. A compound according to claim 1 wherein such compound is cyclopentyl 2-methyl-4-(4-oxo-2-phenyl-4H-thiochromen-8-yl)-5-oxo-1,4,5,7-tetrahydrofuro[3,4-b]pyridine-3-carboxylate of the formula

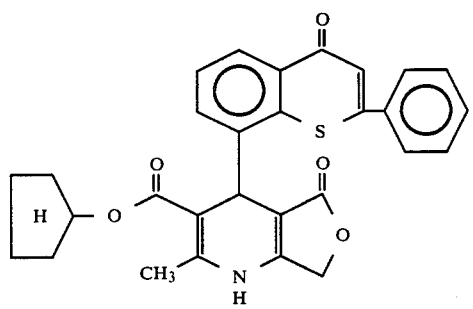

or a pharmaceutically acceptable salt thereof.

9. A compound according to claim 1 wherein such compound is methylthioethyl 2-methyl-4-(4-oxo-2-phenyl-4H-thiochromen-8-yl)-5-oxo-1,4,5,7-tetrahydrofuro[3,4-]pyridine-3-carboxylate of the formula

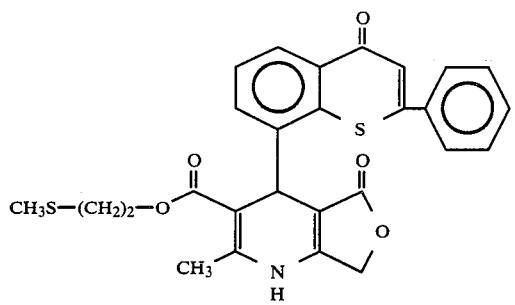

or a pharmaceutically acceptable salt thereof.

10. A circulation-active composition comprising a circulation affecting effective amount of a compound or salt according to claim 1 in admixture with a diluent.

11. A unit dose of a composition according to claim 1 in the form of a tablet, ampule or capsule.

12. A method of modifying the circulation of a patient which comprises administering to such patient a circulation affecting effective amount of a compound or salt according to claim 1.

13. The method according to claim 11, wherein such compound is ethyl 2-methyl-4-(4-oxo-2-phenyl-4H-thiochromen-8-yl)-5-oxo-1,4,5,7-tetrahydrofuro[3,4-b]pyridine-3-carboxylate, methyl 2-methyl-4-(4-oxo-2-phenyl-4H-thiochromen-8-yl)-5-oxo-1,4,5,7-tetrahydrofuro[3,4-b]pyridine-3-carboxylate, n-octyl 2-methyl-4-(4-oxo-2-phenyl-4H-thiochromen-8-yl)-5-oxo-1,4,5,7-tetrahydrofuro[3,4-b]pyridine-3-carboxylate, isopropyl 2-methyl-4-(4-oxo-2-phenyl-4H-thiochromen-8-yl)-5-oxo-1,4,5,7-tetrahydrofuro[3,4-b]pyridine-3-carboxylate, cyclopentyl 2-methyl-4-(4-oxo-2-phenyl-4H-thiochromen-8-yl)-5-oxo-1,4,5,7-tetrahydrofuro[3,4-b]pyridine-3-carboxylate, or methylthioethyl 2-methyl-4-(4-oxo-2-phenyl-4H-thiochromen-8-yl)-5-oxo-1,4,5,7-tetrahydrofuro[3,4-b]pyridine-3-carboxylate, or a pharmaceutically acceptable salt thereof.

* * * * *

UNITED STATES PATENT AND TRADEMARK OFFICE
CERTIFICATE OF CORRECTION

PATENT NO. : 4,555,512
DATED : November 26, 1985
INVENTOR(S) : Siegfried Goldmann, et al.

It is certified that error appears in the above-identified patent and that said Letters Patent is hereby corrected as shown below:

Title Page, Abstract, line 2; Col. 1, line 24; Col. 14, line 53
Col. 4, line 67
Col. 6, line 9

Bottom left of structure delete "$R^3$" and substitute --$R^5$--
After "$R^2$" insert --A--
Middle right of structure delete "A-R'" and substitute --A-$R^1$--
Left side of formula delete "-H$_3$C-" and substitute -- -H$_2$C- --

Col. 12, Example 17, under "$R^4$" and Col. 12, Example 18, under "$R^4$"
Col. 16, lines 46, 47

Col. 18, line 68

Delete "-Chd6-" and substitute -- -C$_6$- --
After "[3,4-" insert --b--

Signed and Sealed this

Eleventh Day of March 1986

[SEAL]

Attest:

DONALD J. QUIGG

Attesting Officer

Commissioner of Patents and Trademarks